United States Patent
Edwards et al.

(10) Patent No.: US 9,102,910 B2
(45) Date of Patent: Aug. 11, 2015

(54) BIOREACTOR

(75) Inventors: Wade Edwards, Fish Hoek (ZA); Winston Daniel Leukes, Grassy Park (ZA); P. G. Lourens, legal representative, Cape Town (ZA)

(73) Assignee: Synexa Life Sciences (Proprietary) Limited, Cape Town (ZA)

( * ) Notice: Subject to any disclaimer, the term of this patent is extended or adjusted under 35 U.S.C. 154(b) by 0 days.

(21) Appl. No.: 13/449,969

(22) Filed: Apr. 18, 2012

(65) Prior Publication Data

US 2012/0322142 A1    Dec. 20, 2012

Related U.S. Application Data

(62) Division of application No. 12/296,889, filed as application No. PCT/IB2007/000765 on Mar. 27, 2007, now abandoned.

(30) Foreign Application Priority Data

Apr. 12, 2006 (ZA) ................................ 2006/02976

(51) Int. Cl.
*C12M 1/00* (2006.01)
*C12M 1/04* (2006.01)

(52) U.S. Cl.
CPC ............... *C12M 29/16* (2013.01); *C12M 23/24* (2013.01); *C12M 23/34* (2013.01)

(58) Field of Classification Search
CPC ....... C12M 23/24; C12M 29/16; C12M 23/34
USPC ...................................... 435/297.2; 210/651
See application file for complete search history.

(56) References Cited

U.S. PATENT DOCUMENTS

| 4,933,084 A | 6/1990 | Bandel et al. |
| 5,945,002 A | 8/1999 | Leukes et al. |

(Continued)

FOREIGN PATENT DOCUMENTS

| CN | 1511792 | 7/2004 |
| CN | 1732256 | 2/2006 |

(Continued)

OTHER PUBLICATIONS

Chinese Office Action for Application No. 200780020367.8, 11 pages, dated Mar. 24, 2011.

(Continued)

*Primary Examiner* — Nathan Bowers
*Assistant Examiner* — Gautam Prakash
(74) *Attorney, Agent, or Firm* — Nelson Mullins Riley & Scarborough LLP; Anthony A. Laurentano (57) ABSTRACT

The present invention relates to a bioreactor comprising a first fluid distribution chamber and a first fluid collection chamber, the reactor adapted to receive at least one conduit in fluid communication between the first fluid distribution chamber and the first fluid collection chamber; wherein the reactor includes a second fluid distribution means including a plurality of distributors arranged to distribute the second fluid between the first fluid distribution chamber and the first fluid collection chamber. The invention extends to a removable insert for a bioreactor comprising a first fluid distribution plate; a first fluid collection plate; and a second fluid distribution means including a plurality of distributors arranged to distribute the second fluid between the first fluid distribution plate and the first fluid collection plate.

12 Claims, 9 Drawing Sheets

(56) References Cited

U.S. PATENT DOCUMENTS

| | | |
|---|---|---|
| 6,620,319 B2 | 9/2003 | Behmann et al. |
| 6,752,926 B2 | 6/2004 | Christodoulatos et al. |
| 2002/0187546 A1 | 12/2002 | Rozga et al. |
| 2004/0191855 A1 | 9/2004 | Leukes et al. |
| 2006/0127971 A1 | 6/2006 | Giordano et al. |

FOREIGN PATENT DOCUMENTS

| | | |
|---|---|---|
| EP | 0398083 A1 | 11/1990 |
| WO | 00/78932 A1 | 12/2000 |

OTHER PUBLICATIONS

International Search Report for Application No. PCT/IB2007/000765, 3 pages, dated Aug. 29, 2007.

BIOREACTOR

RELATED APPLICATIONS

This application is a divisional of U.S. application Ser. No. 12/296,889, filed Aug. 20, 2009 (now abandoned), which is a 35 U.S.C. 371 national stage filing of International Application No. PCT/IB2007/000765, filed Mar. 27, 2007, which claims priority to South African Application No. 2006/02976 filed on Apr. 12, 2006. The contents of the aforementioned applications are hereby incorporated by reference.

BACKGROUND OF THE INVENTION

This invention relates to a bioreactor. In particular this invention relates to a bioreactor including membrane conduits and being adapted to received a first and second fluid.

In the biotechnology and biopharmaceutical industry, the most relevant bio-origin compounds are produced using bio-processes involving specific cell culture systems operated and controlled within a cell culture bioreactor or module.

In general, these cell-culturing systems are characterized by several process limitations as well as fundamental physical constraints delimiting the maximal production capacity of these established generic technologies. These limitations are expressed fundamentally as limits in mass transfer capabilities of these technologies. Examples of such known technologies include pneumatic reactors, solid state reactors and membrane conduit bioreactors.

It is obvious that the limitations mentioned above have a negative impact on the cost-effectiveness of these reactors and on the efficacy with which they function.

Furthermore, usually a specific process demands a specific type of reactor and therefore it can be extremely costly to have to purchase new process-specific reactors as they are required.

A need exist for an improved bioreactor.

A further need exists for improved reactors which are either adapted to the purpose required or which can be adapted to such purpose in a commercially viable manner.

SUMMARY OF THE INVENTION

According to a first aspect to the present invention there is provided a bioreactor comprising:
  a first fluid distribution chamber; and
  a first fluid collection chamber, the reactor adapted to receive at least one conduit in fluid communication between the first fluid distribution chamber and the first fluid collection chamber;
wherein the reactor includes a second fluid distribution means including a plurality of distributors arranged to distribute the second fluid between the first fluid distribution chamber and the first fluid collection chamber.

The bioreactor may include a plurality of conduits in fluid communication between the first fluid distribution chamber and the first fluid collection chamber. The conduits are preferably membrane conduits. In a preferred embodiment of the present invention the conduits are axially elongate having first and second ends (resembling drinking straws). Such conduits are described in U.S. Pat. No. 5,945,002 (Leukes et al.) and US Publication No. 2004/0191855 A1 (Leukes et al.), the contents of both of which are included herein by reference.

The first end of the conduits are preferably adapted to engage in the first fluid distribution chamber and the second end of the conduit is adapted to engage with the first fluid collection chamber.

The first fluid may be a liquid, for example a liquid nutrient. The second fluid may be a gas, for example, oxygen, nitrogen or a mixture thereof.

Preferably the distributors distribute the second fluid amongst the conduits. The distributors preferably distribute the second fluid in a direction transverse to a longitudinal axis of the conduits. The distributors preferably extend between the first fluid distribution chamber and the first fluid collection chamber and may be substantially parallel with the conduits. There are preferably at least two distributors, more preferably at least three distributors, more preferably at least four distributors, more preferably at least five distributors, more preferably at least six distributors, more preferably at least seven distributors and more preferably at least eight distributors.

The chambers preferably include perforated plates. The conduits may engage with or within the perforations. The conduits may engage by epoxy sealants and/or clamping plates.

The chambers are preferably spaced from each other with the conduits extending between them.

The bioreactor may include a skin defining a lumen between the chambers. The bioreactor may include a second outer skin. The outer skin may be adapted to receive temperature modifying fluids in a space between the two skins.

The second fluid distribution means preferably includes a chamber. The second fluid distribution means may include a manifold.

The bioreactor may include spacer means, for example, bars separating the first fluid distribution chamber from the first fluid collection chamber.

In one embodiment of this aspect of the present invention the perforated plates, conduits and second fluid distribution means comprise a removable insert. The insert may engage with a framework of the bioreactor.

According to a second aspect to the present invention there is provided a removable insert for a bioreactor comprising
  a first fluid distribution plate;
  a first fluid collection plate; and
  a second fluid distribution means including a plurality of distributors arranged to distribute the second fluid between the first fluid distribution plate and the first fluid collection plate.

According to a third aspect to the present invention there is provided a bioreactor comprising a frame adapted to receive a removable insert, the bioreactor comprising a first fluid inlet and distribution means, a second fluid inlet and distribution means, a first fluid collection means and outlet and a second fluid outlet.

Preferably the second fluid distribution means includes a plurality of distributors arranged to distribute the second fluid between the first fluid distribution plate and the first fluid collection plate.

Preferably the removable insert comprises a lumen and means for effecting fluid communication between the first fluid distribution means and first fluid collection means. The means for effecting fluid communication is preferably a conduit, most preferably a membrane conduit. In a preferred embodiment of the present invention the conduits are axially elongate having first and second ends (resembling drinking straws). The first end of the conduits are adapted to engage in the first fluid distribution means and the second end of the conduit is adapted to engage with the first fluid collection means.

The first fluid distribution means preferably comprises a distribution reservoir (chamber) defined by the frame, a distribution plate and a base. The distribution plate defines at least one perforation in which a first end of the membrane conduits is adapted to engage. The same is true for the first fluid collection means which preferably comprises a collection reservoir (chamber) defined by the frame, a collection plate and a cap. The collection plate defines perforations into which the second ends of the conduits engage. It will be appreciated that the ends of the membrane conduits may first be engaged, co-axially or otherwise, in pots or the like which in turn engage with the perforations in the distribution or collection plates. Epoxy sealants may also be used. In addition, sealing plates may also be used The cap and the base are preferably removably attachable to the frame and/or insert and may be configured to accommodate the first and/or second fluid inlets and/or outlets.

The distribution plate and/or the collection plate are preferably included on the insert.

In a preferred embodiment, the first fluid inlet is in fluid communication with the distribution reservoir. Similarly, the first fluid outlet is in fluid communication with the collection reservoir. In use the first fluid enters the distribution reservoir via the first fluid inlet, passes through the perforations in the distribution plate, through the membrane conduits, through the perforations in the collection plate and into the collection reservoir where the first fluid exits the bioreactor via the first fluid outlet.

Preferably the first fluid is a liquid, for example a liquid (nutrient) medium suitable to sustain growth of micro-organisms and the second fluid is a gas, for example air. Examples of micro-organisms which may be sustained by the medium include bacteria and fungi including but not limited to *Streptomyces coelicolor* (aerobic process mode) and *Lactococcus lactis* (anaerobic process mode).

The membrane conduits may be comprised of a polymer material or a ceramic material. Preferably the conduits are comprised of a ceramic material, more preferably $Al_2O_3$. This allows for autoclave sterilization, and chemical (for example $H_2O_2$) cleaning without damage to the membrane conduits or housing. The membrane conduits are typically rigid (as opposed to flexible, in the case of polymer membrane conduits), which facilitates assembly of the insert and bioreactor, whereby touching of the membrane conduits can be minimised. The ceramic membrane conduit wall allows for good attachment of micro-organisms (as hereinbefore described), and the environment might stimulate differentiation in soil adapted organisms.

Preferably a plurality of the membrane conduits join the first fluid distribution and collection means. The membrane conduits may be pre-selected depending on the particular application of the bioreactor. Consistent spacing of the membrane conduits may be accurately achieved, and the spacing may be optimized for each application. Spacing of the membrane conduits is effected by suitable placing of perforations in the distribution and collection plates.

Preferably the second fluid distribution means is included within the removable insert. The second fluid distribution means preferably comprises a manifold in fluid communication the second fluid inlet and with fluid distributors located within the lumen of the insert. The fluid dispensing means may be at least one axially extending conduit positioned adjacent and preferably substantially parallel the membrane conduit(s). The fluid distributors may be adapted to effect transverse movement of the second fluid relative to a longitudinal axis of the membrane conduit(s). This may be achieved by a series of outlets located along the length of the fluid distributors. The outlets are preferably dimensioned such that substantially equal entry velocities of the second fluid into the insert lumen is effected across all outlets of the fluid dispensing means. Alternatively, the outlets may be so dimensioned such that substantially equal exit velocities of the second fluid from the distributors is effected across the outlets.

This may be achieved by making the outlets such that the resistance provided by the outlet is substantially greater than the resistance between each outlet.

The insert may include or be contained within a sleeve. The sleeve preferably allows visual inspection of the membrane conduits.

BRIEF DESCRIPTION OF THE DRAWINGS

The invention will now be described in more detail, by way of example only, with reference to the following drawings.

DETAILED DESCRIPTION OF PREFERRED EMBODIMENTS

Figure 1:
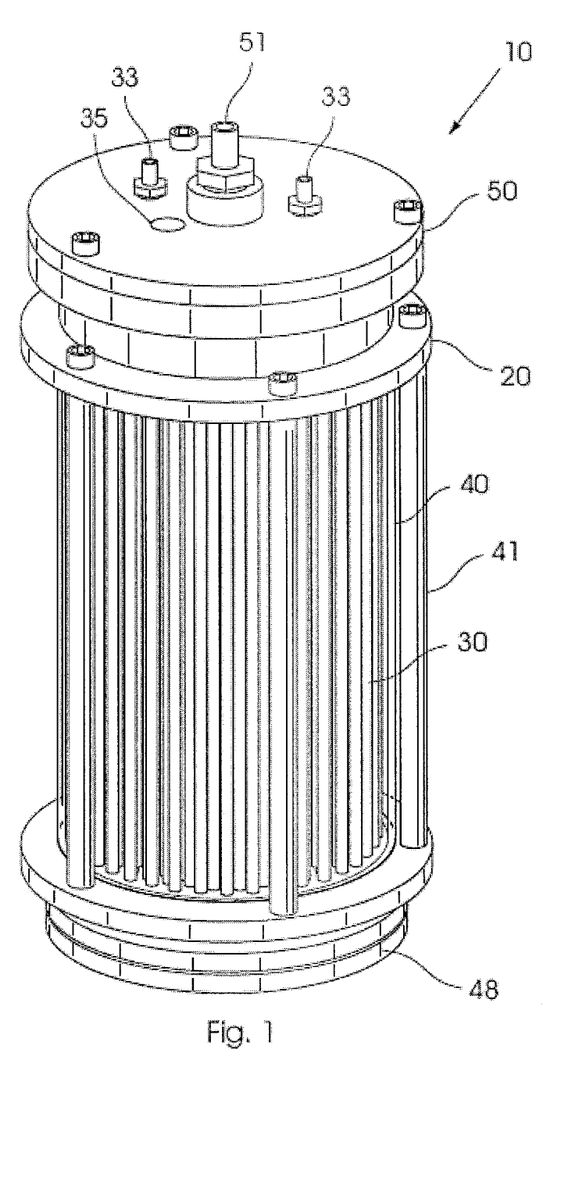
FIG. 1 shows a perspective view of the bioreactor according to the present invention, from the top and one side.

According to the invention, as illustrated in FIG. 1, a bioreactor 10 comprises a frame 20 adapted to receive a removable insert 30. The bioreactor 10 comprises a first fluid inlet 31 and distribution means 32, a second fluid inlet 33 and distribution means 34, first fluid collection means 44 and outlet 35 and a second fluid outlet 36.

The first fluid distribution means 32 comprises a distribution reservoir 47 defined by the frame 20, a distribution plate 38 and a base 48.

The first fluid collection means 44 comprises a collection reservoir 49 defined by the frame 20, a collection plate 39 and a cap 50.

The cap 50 and the base 48 are removably attachable to the frame 20 and are configured to accommodate the first and/or second fluid inlets 31, 33 and/or outlets 35, 36.

The removable insert 30 comprises means for effecting fluid communication between the first fluid distribution means 32 and first fluid collection means 44 in the form of a plurality of membrane conduits 37. The conduits 37 are axially elongate having first and second ends. The first end of the conduits 37 are adapted to engage in the perforations of the distribution plate 38 and the second end of the conduit 37 is adapted to engage in the perforations of the collection plate 39.

Figure 2:
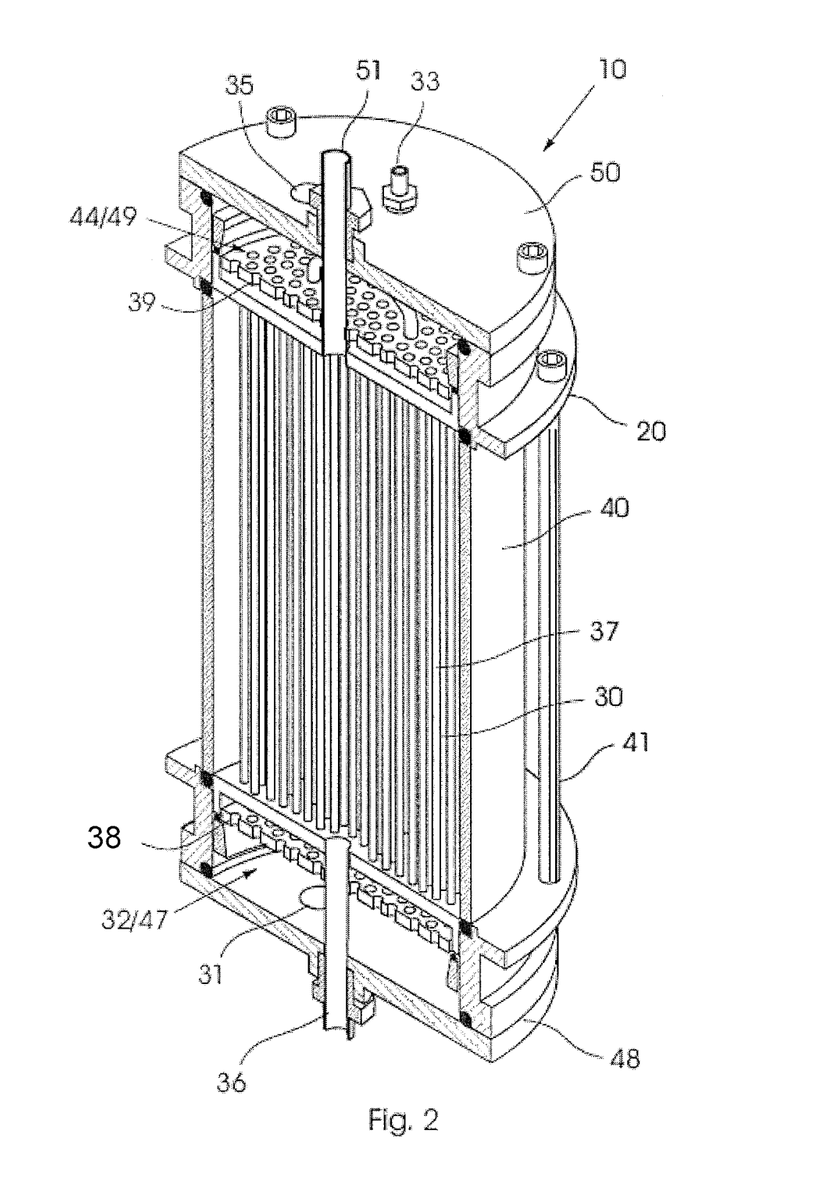
FIG. 2 shows a cross sectional view of the bioreactor according to the present invention.

The insert 30 may include or be contained within a sleeve 40 as shown in FIG. 2. The sleeve 40 may be made of any suitable material such as glass, stainless steel or the like. Glass is particularly suitable as it has a good chemical compatibility and has good temperature stability as well allowing for visual inspection of the membrane conduits. A material such as stainless steel may be used for high pressure applications. The frame 20 of the bioreactor 10 includes removable supporting means 41 for fixing the first fluid distribution means 32 and the first fluid collection means 44 in position. The supporting means 41 may be at least one bar or the like. The supporting means 41 enables ready and uncomplicated insertion of the removable insert 30 into the frame 20.

Figure 3:
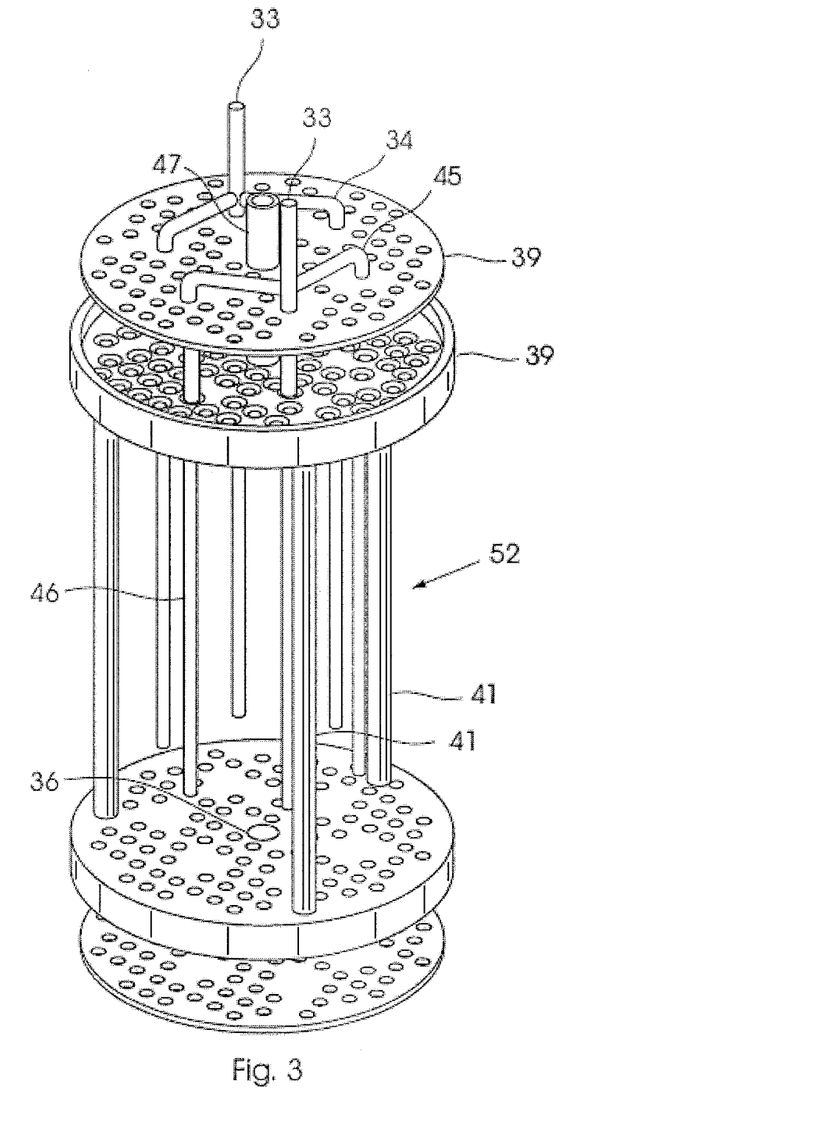
FIG. 3 shows a perspective view of the removable insert according to the present invention, from the top and one side.
Figure 4:
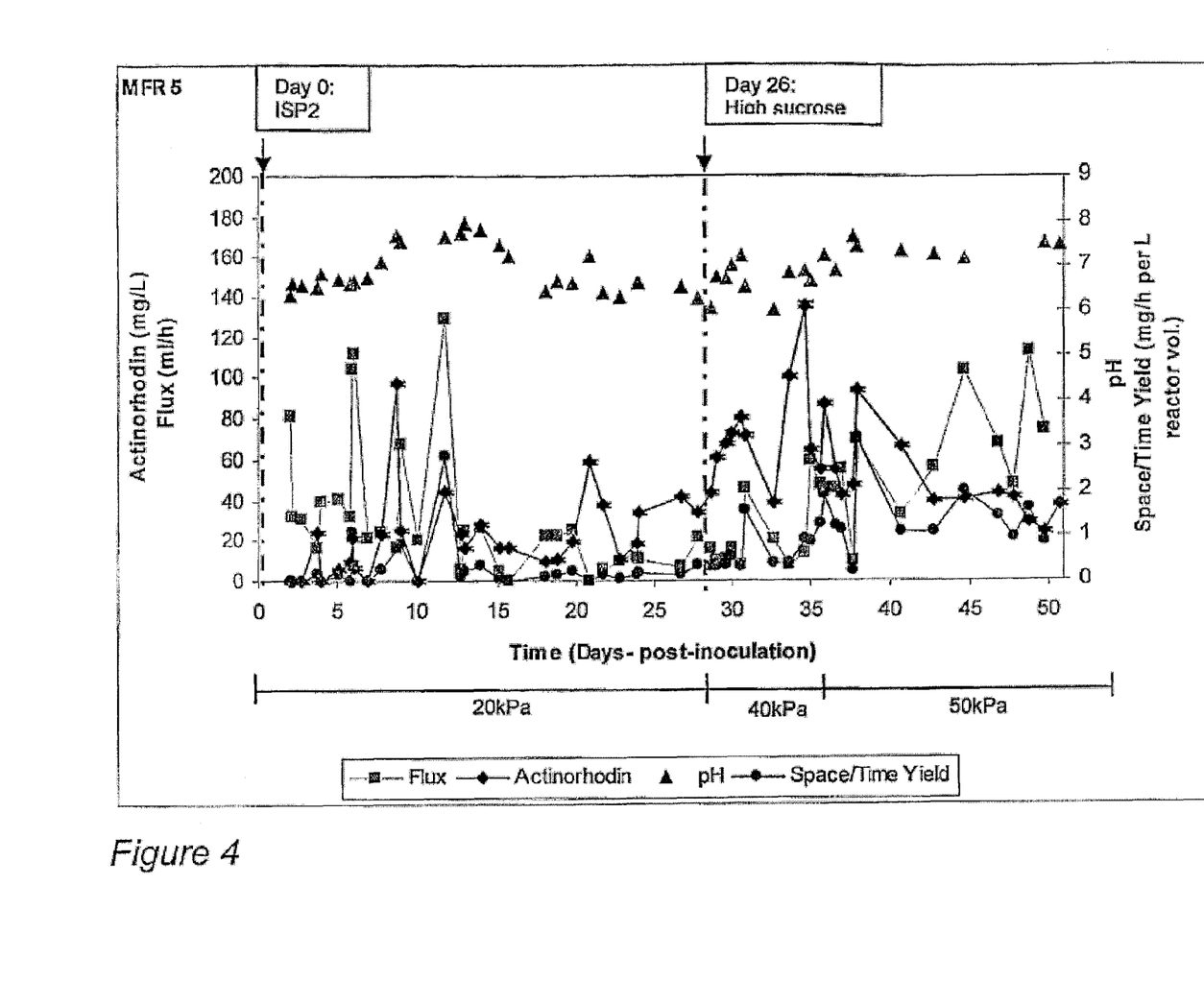
FIG. 4 shows the time-course production of actinorhodin by *S. coelicolor* using an MFR.

In use, the removable insert 30 as shown in FIG. 3 is specifically positioned and both hydraulically and pneumatically sealed within the frame 20 using a locking means such as floating threaded lock-rings which enable the insert 30 to then be mechanically sealed against the frame 20. Mechanical sealing may be achieved by mechanical seals such as silicone rubber based o-rings or the like. The locking means and the mechanical seals enable the membrane conduits 37 to be mechanically separated from the first fluid distribution means 32 and the first fluid collection means 44. The first fluid distribution means 32 and the first fluid collection means 44 may also be sealed in a similar manner against the frame 20 so that they are fluid-tight. The first fluid is passed into the first fluid distribution reservoir 47 and through the perforations in the distribution plate 38. The first fluid flows through the membrane conduits 37, through the perforations in the collection plate 39 and into the first fluid collection reservoir 49. The first fluid may then exit the first fluid collection reservoir via the outlet 35.

The first fluid distribution plate 38 and collection plate 39 may be as illustrated in FIG. 2. The distribution plate 38 enables equal entry velocities from the distribution reservoir 47 into the membrane conduits 37 across the spatial arrangement of the membrane conduits 37 within the insert 30. It will be appreciated that the distribution means 32 may consist of more than one plate or the like depending on the particular bioreactor, as illustrated in FIG. 3. A second plate may be used as a pressure plate when mechanically sealing membrane conduits within the distribution plate 38 and/or collection plate 39 using O-rings or the like. In the absence of the second plate membranes may be sealed within the distribution plate 38 and/or collection plate 39 using resin or other means whereby the second pressure plate is no longer required.

The first fluid distribution plate 38 and the first fluid collection plate 39 as well as the frame 20 of the bioreactor 10 are typically made of stainless steel or the like. This material typically allows for high chemical compatibility and preferably the surface finish of the steel is less than about 0.22 μm.

Typically the first fluid is a liquid and the second fluid is a gas, preferably air. The bioreactor would then typically be a gas-liquid contactor which permits the required reticulation for Membrane Biofilm Reactor operation. However, the bioreactor may also be a liquid-solid contactor with a high mass transfer of liquid to a biofilm growing on an outside surface of the membrane conduits. This would usually be the configuration used for the anaerobic secondary metabolite and recombinant protein production process.

In FIG. 2, the arrangement of the membrane conduits 37 is shown in more detail. Preferably a plurality of membrane conduits 37 join the first fluid distribution 32 and collection means 44. The configuration of the membrane conduits 37 in the insert 30 is typically dependent on and determined by the configuration of the distribution plate 38. This variable configuration allows the insert 30 to be flexible with regards to the membrane conduit type/form 37. Furthermore, it enables the spacing of the membrane conduits 37 to be accurately determined and it is easier to maintain consistent spacing between the membrane conduits 37. This is normally difficult to achieve in large scale manufacturing of commercially available reactor modules and as a result the membrane conduits are often arranged in random bundles which is not optimal for the growth of various micro-organisms. In the present invention, it is easier to optimise the spacing of the membrane conduits 37 for each particular application. For example, when thick bio-films are generated, it is usually more advantageous to have wider spacing between the membrane conduits 37. The membrane conduits 37 may be pre-selected depending on the insert 30 used and on the particular application.

The membrane conduits 37 may take the form of tubular membrane conduits, capillary membrane conduits, hollow-fibre or the like.

The membrane conduits 37 may be made of ceramic material, preferably $Al_2O_3$, or any other suitable material. This allows for (steam) autoclave sterilization, and chemical cleaning without damage to the membrane conduits or housing. The membrane conduits 37 are typically rigid (as opposed to flexible, in the case of polymer membrane conduits), which allows for easy assembly, with minimal touching of membrane conduits 37. The ceramic membrane conduit wall allows for good attachment of micro-organisms, and the environment might stimulate differentiation in soil adapted organisms.

The advantages of having a removable insert are numerous. Firstly, with conventional reactors, if a membrane conduit breaks or cracks, often the whole reactor needs to be replaced. However, according to the present invention, the membrane conduit may be easily replaced without any significant delays in the process. Further, inserts sealed mechanically with a pressure plate as illustrated in FIG. 3 allow for individual membranes to be replaced and inserts to be recycled more easily than if a resin based sealant were used. This would obviously result in decreased turn around time for repairs and maintenance. Secondly, the inserts are easily interchangeable depending on the application, as opposed to many reactors that are known in the art which are specifically produced for a single application. Having a reactor that could be used for multiple applications, depending on the insert used, would be very cost effective and efficient. Thirdly, as the inserts are removable, cleaning of the reactor is much easier. The removable insert therefore provides flexibility of use for application to different organisms that may require different membrane conduit spacing or other applications of the bioreactor including but not limited to membrane filtration for perfusion systems. In addition, the bioreactor assembly is such that the inserts are interchangeable, can be easily removed after use for cleaning or may be changed for optimal arrangement.

As illustrated in FIGS. 2 and 3, the means for distributing the second fluid 34, typically a gas such as air, within the insert 30 preferably comprises a manifold 45 in fluid communication with distributors 46 located within the lumen 52 of the insert 30. The manifold 45 and/or distributors 46 is/are integrally formed with the insert 30. This allows the insert 30 to be made of several different material types as the distributors are part of the insert structure and are not attached to the insert at a later stage.

The distributors 46 are conduits positioned adjacent and substantially parallel with at least one membrane conduit 37 (not shown in FIG. 3). The distributors 46 are adapted to effect transverse movement of the air relative to the axial lengths of the membrane conduits 37. This may be achieved by a series of outlets (not shown) located along the length of the distributors 46.

The outlets are preferably dimensioned such that substantially equal entry velocities of the air across all outlets is effected into the insert 30. Thus the flow of air from each outlet is typically substantially the same. This may be achieved by making the outlets such that the resistance provided by the outlet is substantially greater than the resistance between each outlet. Furthermore, the arrangement of the distributors 46 in the insert 30 is such that the flow of the air is evenly spread/distributed around the membrane conduits 37 (see FIGS. 7A and 7B).

The distributors 46 can be manufactured in such a way so as to increase or to decrease the number of outlets along the length of the distributors 46 according to the particular application for which the bioreactor is used. The fluid flow of the air via the outlets across the membrane conduits 37 typically increases turbulence at low second fluid flow rates which facilitates a high second fluid mass transfer at low energy transfer rates. When the second fluid is air, the mass transfer is preferably oxygen mass transfer. Fluidic communication between the typically liquid phase (e.g. liquid medium) within the membrane conduits and the typically gaseous phase (e.g. air) within the insert is achieved using a differential pressure gradient across the membrane conduits 37. This pressure gradient typically necessitates pneumatic and hydraulic sealing of various compartments of the bioreactor 10.

The recirculation of the air at the top of the insert then facilitates energy transfer when the air is heated to provide an incubation temperature conducive to cell growth. The flow of air transverse to the orientation of the membrane conduits 37 would typically allow for good oxygen mass transfer. This could result in larger bioreactors having as good an oxygen mass transfer as smaller bioreactors without oxygen limitation. The distributors 46 may be tailor made to suit the requirements of a particular application or reactor size so that sufficient fluid (aft) is provided.

Typically, the first and second ends of the bioreactor 10 are non-interchangeable. This is due to the Insert 30 configuration, as shown in FIGS. 1, 2 and 3, where the distributors 46 pass through the first end of the insert 30 and are positioned at the upper end of the bioreactor 10 only. In this instance, the distributors 46 do not pass through the entire insert 30 and the second end of the insert/frame/bioreactor. This preferential assembly configuration minimizes the number of seals necessary to seal the various components of the bioreactor 10 and therefore minimizes possible contamination access points. However, it will be appreciated that further embodiments may include interchangeable ends and therefore the present invention is not limited to the embodiment described above.

The bioreactor 10 is typically constructed from materials that allow steam sterilization and cleaning with harsh chemicals such as solvents, caustic and oxidizing agents. The bioreactor height is determined to be such that, based on the porosity and operating fluid flow rates used, resistance to flow offered to the first fluid stream is such that permeation along the entire length of the membrane conduit 37 is facilitated. In addition, the membrane conduits are not too long such that the first fluid flow path in the vertical operation in the aerobic culturing mode is suboptimum for growth (i.e. the biofilm becomes too heavy and collapses) and product formation (i.e. the torroidal flow path is so extended that metabolic waste products inhibit the biomass at the bottom end of the bioreactor).

In use, the bioreactor 10 is placed in a substantially vertical arrangement with the first fluid inlet 31 typically at the base of the reactor and the second fluid inlet 33 typically at the top of the bioreactor 10. A biofilm is established on an external surface of the membrane conduits 37, which may be capillary membrane conduits. This is achieved by reverse filtering a spore or vegetative inoculum of the desired micro-organism through the membrane and draining any permeate out the lumen 52 of the insert 30 into the lumen of membrane conduits 37 exiting through the first fluid outlet 35. The inoculum is thus immobilised on the membrane surface.

An appropriate nutrient medium for the micro-organism is then supplied into the membrane conduits 37 so as to perfuse through the conduits and into the lumen 52 of the insert 30 continuously at a rate sufficient to allow growth to occur in the biofilm established on the surface. The nutrient medium which passes through the membrane conduits 37 enters the collection reservoir 49 and exits through the outlet 35 and may be pumped back and recycled through the distributions means 32 of the insert 30. Some of the nutrient medium permeates through the membrane forming permeate droplets on the biofilm and running down the biofilm. Humidified air is fed into the insert 30 by means of the distributors 46 and vented through the outlets 36 and 51. Outlet 51 may be closed off or kept open, depending on the application of the bioreactor. Preferably the outlet includes a pressure gauge (not shown) to enable the pressure in the bioreactor to be monitored. Any product of the biofilm is collected in the nutrient medium permeate which is removed from the reactor lumen 52 along with the second fluid through the outlet 36.

The air that is blown through the bioreactor 10 serves to supply the oxygen that is required for viability of the biofilm, and also to carry away spores and dead cells that are shed from the outer surface of the biofilm.

When operating the bioreactor as a liquid solid contactor the nutrient medium is supplied to the biofilm through second fluid distributors 46. The reactor lumen 52 is filled with growth medium and the biofilm is immobilised on the surface of membrane conduits 37 as the flow passes through the biofilm into the lumen of the conduit 37 as described during inoculation process for aerobic operation above. The permeate exits through the first fluid distribution 32 or collection means 44 and is collected from the first fluid inlet 31 or outlet 35 means. This enables microaerophillic or anaerobic growth of a biofilm with increased mass transfer of nutrients to the biofilm and the continuous removal of metabolic waste and/or product.

Figure 5A:
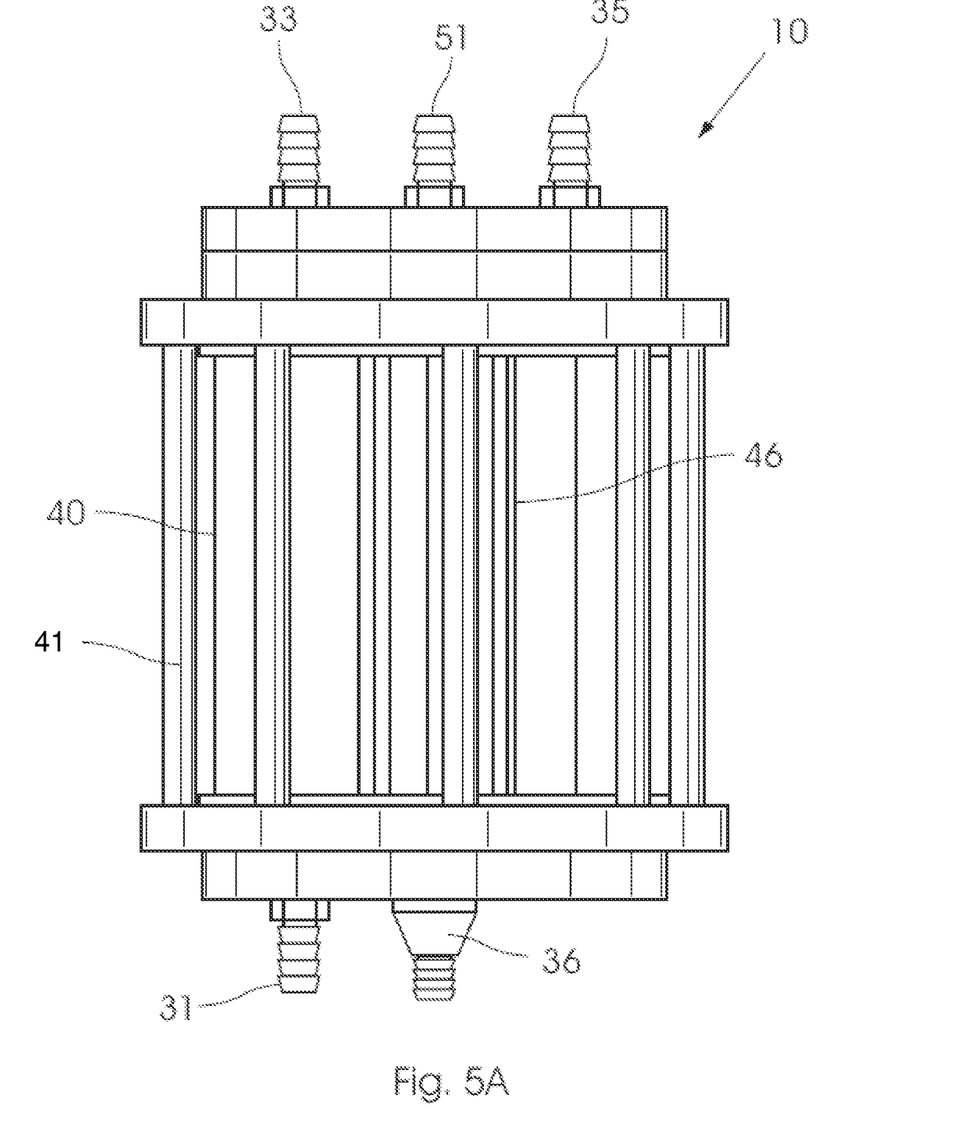
FIG. 5A shows a side view of an assembled bioreactor according to one aspect of the present invention.
Figure 5B:
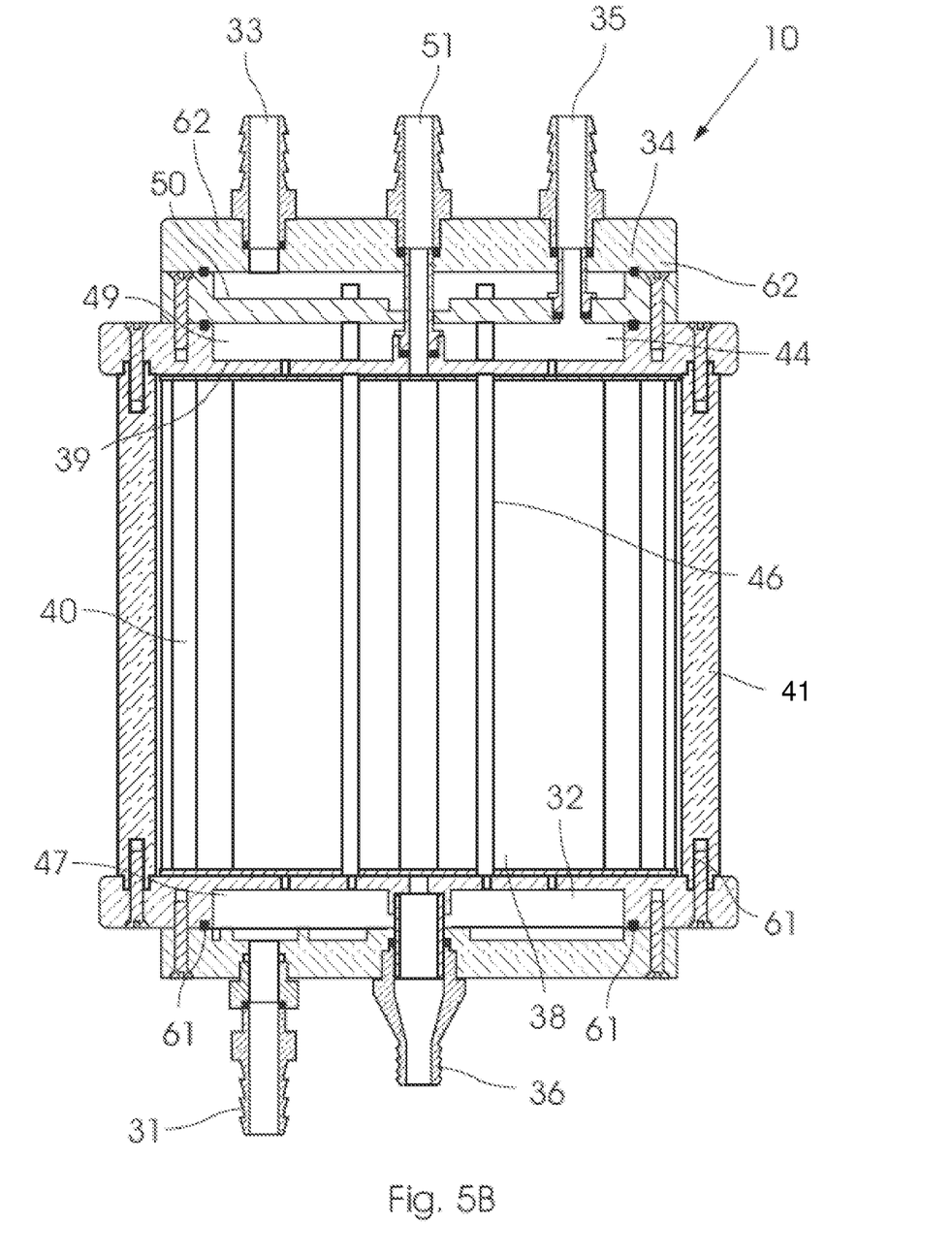
FIG. 5B shows a cross section through the view of FIG. 5A.
Figure 6:
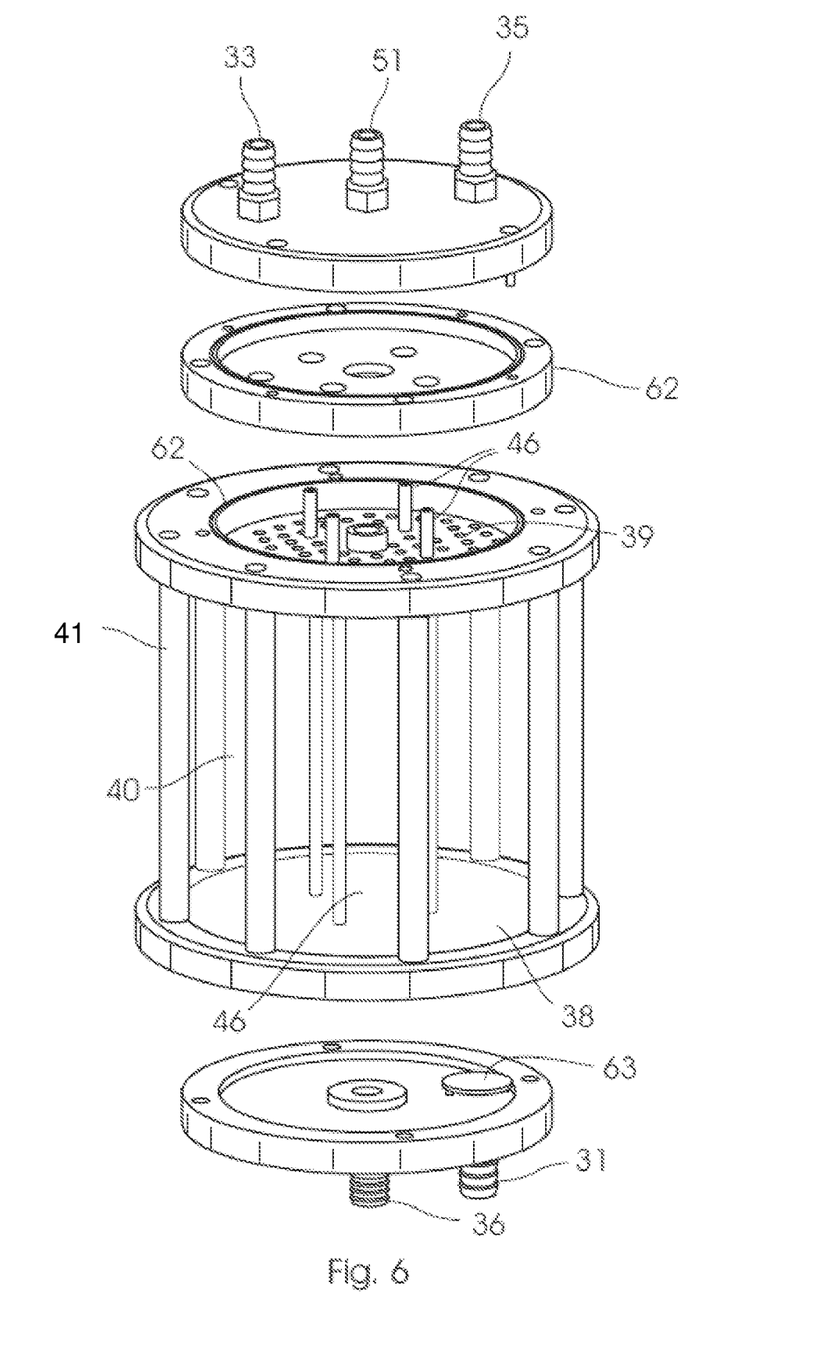
FIG. 6 shows an exploded view of the bioreactor according to one aspect of the present invention.

FIGS. 5A, 5B and 6 show an alternative embodiment of the bioreactor according to the present invention (conduits not shown). In these figures the bioreactor is a sealed unit which may be sold preassembled to suit a particular purpose. In such an embodiment the bioreactor includes spacer bars spacing the first fluid distribution chamber (reservoir) 47 from the first fluid collection chamber (reservoir) 49.

Components of the bioreactor are secured together by way of hex screws 61 and interfaces between components are rendered fluid (gas) tight by way of O-ring seals 62.

In FIG. 6 a first fluid interrupter plate 63 is located adjacent the first fluid inlet 31 to obfuscate an entry vector of the first fluid resulting in its improved distribution within the first fluid distribution chamber 47.

Figure 7A:
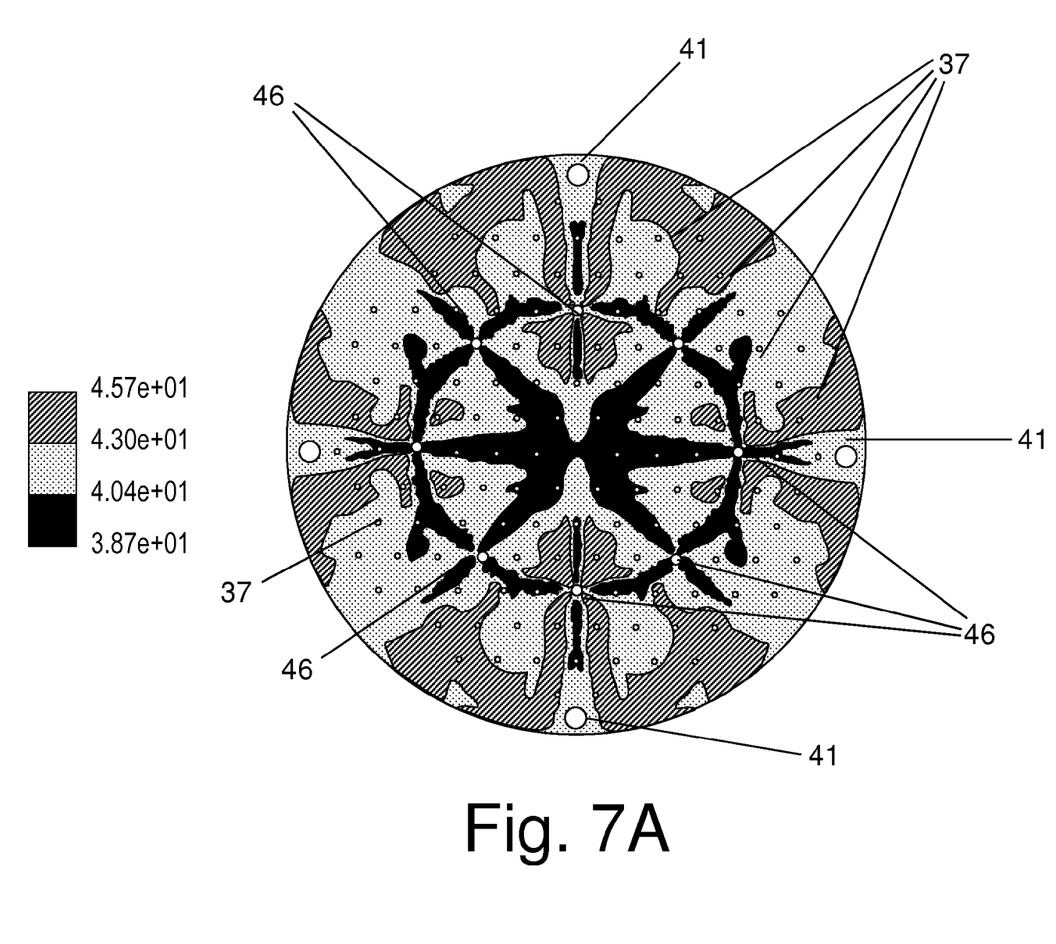
FIGS. 7A and 7B show a cross section plan view of the second fluid distribution pattern within the bioreactor, both with and without a biofilm present on the membrane conduits.
Figure 7B:
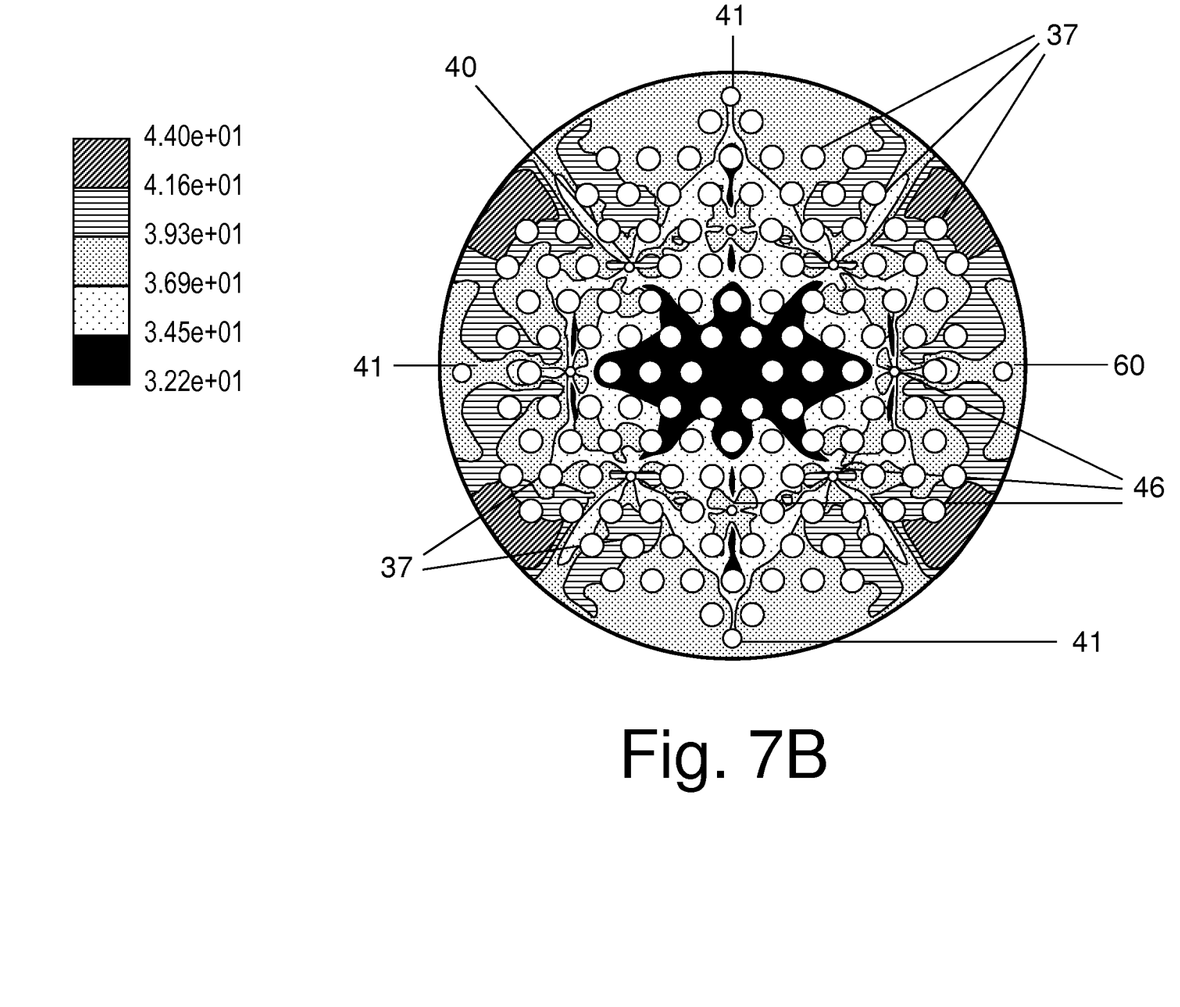

In FIGS. 7A and 7B LMA (local mean age) simulations are analogous to simulated residence time distribution analysis.

The simulation outcome enables analysis of variations in exiting air molecule age to be determined. Significant differences indicate areas within the designed volume where unequal flow and/or conditions of laminar and turbulent flow are generated or exist (where Reynolds numbers (Re) are significantly above or below 2000 within the same volume being analyzed).

In situations where Re of >> and << 2000 exist, the premise that the organism is in a low shear environment (an advantage inherent to the present invention), is void. The computational fluid dynamic (CFD) simulations indicate that the design takes this into account and because all LMA values are more or less within 7-10 seconds of each other indicates that the velocity profiles are similar and shows that the environment around the organism is indeed more homogenous than heterogenous—these conditions were analysed insofar as the hardware was concerned (all conditions indicated as 'no biofilm') as well as taking into account the possible increased air flow (and possibly channeling) that would be evident with biofilm present on the conduits (all models where a 12 mm biofilm was simulated). The 12 mm biofilm simulated a space restriction from 27 mm between conduits to 3 mm after a predetermined amount of growth.

All simulations were done at a linear air velocity equivalent to 1 volume of air entering and exiting per minute.

The cross section views presented in FIGS. 7A and 7B simulate air inlet jet patterns (4 vector pattern) and whether a simulated biofilm would adversely restrict air passage to any of the areas within the reactor volume.

The invention will now be described with reference to the following non-limiting examples.

EXAMPLE 1

Actinorhodin Production by *Streptomyces coelicolor*

Sterilisation

The MFR module, reticulation, pressure gauges and ancillary equipment/bottles were autoclaved separately and connected one another using sterile technique. The MFR was configured for aerobic operation according to standard operating procedures.

Inoculation

The ECS of the MFR module was filled with approximately 2 L growth medium containing 100 ml of a 3 day *S. coelicolor* flask culture. The mycelial inoculum was immobilized onto the outer surface of capillary membranes under pressure. Spent inoculum was collected from the lumen side of the capillary membranes through the medium outlet or prime line into a collection vessel. Once the entire volume of inoculum within the ECS was drained the reactor was configured for aerobic operation according to standard operating procedures.

Operation

The MFR was incubated at 28° C. and operated aerobically with air flow across the outer surface of the capillary membranes (and biofilm) at a flow rate of 2 L per hour. The air pressure within the ECS was maintained at 20 kPa for the first 26 days and increased to 40 kPa and 50 kPa on days 27 and 36, respectively. The pressure differential between capillary lumen and ECS was used to control flux across the membrane surface and nutrient supply to the biofilm. The medium pressure was manually controlled in order to maintain stable flux as the developing biofilm increased the resistance to nutrient flow, thus influencing flux levels.

The biofilm grew rapidly spreading along each membrane surface, changing from yellow to red in colour before differentiation and sporulation was observed. By day 8 the biofilm was blue-grey with spores and red-black droplets of permeate were visible on the biofilm surface. The coloured permeate containing actinorhodin product was collected via the air and permeate outlet. Actinorhodin level within permeate was quantified spectrophotometrically using a standard operating procedure Based on methods described by Ates et al. 1997 (E1%, 1CM=355).

Summary of Productivity

A total of 1067 mg was produced by the MFR over a 50 day period. Effectively, production was initiated 3 days post-inoculation. Peak production was between days 27 and 50 (coinciding with confluent growth and differentiation of the biofilm) giving a daily production average of 32.3 mg and an average volumetric productivity (Space/Time Yield) of 0.98 mg/h per L reactor volume.

TABLE

Lists the maximum and mean actinorhodin concentration (mg/L) and productivity (mg/h per L reactor vol.) over a 50 day period.

| Actinorhodin (mg/L) | | | Space/Time Yield (mg/h per L reactor vol.) | | |
|---|---|---|---|---|---|
| Maximum | Mean | SD | Maximum | Mean | SD |
| 135.73 | 38.33 | 30.12 | 3.19 | 0.61 | 0.72 |

EXAMPLE 2

The Production of Recombinant β-Lactamase by *Lactococcus lactis* Strain PRA290 Using the P170 Expression System Sterilisation The MFR module, reticulation, pressure gauges and ancillary equipment/bottles were autoclaved separately and connected one another using sterile technique. The MFR was configured for microaerophillic or anaerobic operation according to standard operating procedures.

Inoculation 50 ml of a 15 hr culture of *L. lactis* PRA290 (producing recombinant β-lactamase enzyme under the control of the P170 promotor) was inoculated directly into the ECS of the MFR module. The ECS was filled with LM1 growth medium and operated under recirculatory mode, pumping culture medium from the shell side through the capillary membranes and collecting the permeate from the lumen side. This process enabled immobilization of the biomass on the outer surface of capillary membranes.

Operation

*L. lactis* was cultured in LM1 growth medium containing 200 mM phosphate buffer, pH 7.2. The culture was incubated at 25° C.

Initially the MFR was operated anaerobically in recirculatory mode. During this period samples were taken from the lumen outlet and pH and enzyme activities recorded. After 15 hrs the lumen outlet was disconnected from the nutrient supply vessel and permeate collected in a clean permeate collection vessel. Fresh LM1 growth medium was attached to the MFR and the reactor supplied continuously with fresh nutrients. Flux, pH and enzyme activities of permeate were monitored over time. Flux was manually regulated by changing the pressure supplying the nutrient medium to the MFR at the shell side. As the immobilized biofilm became thicker and resistance against flow increased, the medium pressure was increased stepwise in order to sustain flux levels. Optimal flux was determined by monitoring the pH of permeate, where the flux control strategy was aimed at maintaining the pH within the ECS as close as possible to the optimal pH range (pH 5.5-6.5) for recombinant protein expression under the control of the P170 promotor.

When permeate pH levels were observed to approach pH 4, the β-lactamase activity in permeate was observed to drop and flux levels could no longer be sustained, even at pressures approaching 100 kPa, the experiment was ended.

δ-lactamase activity was quantified spectrophotometrically using a standard operating procedure base on the Nitrocefin method (Oxoid).

Summary of Productivity

Initial β-lactamase levels declined during the first 15 hrs as residual activity of the inoculum was diluted out in the medium supply vessel during recirculation. Further, increased nutrient concentration and dilution of lactic acid produced by *L. lactis*, although optimal for growth, would have negatively effected auto-induction of the P170 expression system controlling β-lactamase production, thus limiting expression of recombinant enzyme. During this 15 hour period approximately 1021 Units of β-lactamase was produced.

After 15 hrs the developing biofilm was apparent as a thin film on the surface of capillary membranes. In changing the MFR operation to continuous supply of fresh nutrient medium at lower flux, optimal conditions for the δ-lactamase expression were achieved (pH 5.5-6.5). From 16-38 hrs post-inoculation a total of 309 Units of δ-lactamase was produced with a maximum titre of 785 U/L. Over this period higher flow rates were maintained, resulting in a maximum volumetric productivity of 19.7 U/h per L reactor volume and a mean of 10.5 U/h per L reactor volume. As the biofilm grew and resistance to nutrient flow increased, sequentially higher pressures were required to sustain flux. During an overnight period when the MFR was not monitored, flux levels declined and permeate pH was reduced to pH 4.5, below the optimal range for expression. By increasing the pressure supplying the nutrient feed, higher flux levels were recovered to an extent but increased biofilm thickness and resistance did not allow for high enough flux levels to stabilize the pH within production range, nor high enough flow rates to prevent planktonic growth of the biofilm (this can result in backgrowth into the nutrient supply vessel). From 39-62 hrs a total of 87 Units β-lactamase was produced with a maximum titre of 400 U/L. Due to low flow rates the volumetric productivity was halved, reaching a maximum of 6.9 U/h per L reactor volume with a mean of 5.3 U/h per L reactor volume.

TABLE

Lists the maximum and mean β-lactamase activity (U/L) and productivity (U/h per L reactor vol.) over a 50 day period.

| Process Time | Units β-lactamase produced | β-lactamase activity (U/L) | | | Space/Time Yield (U/h per L reactor vol.) | | |
|---|---|---|---|---|---|---|---|
| | | Maximum | Mean | SD | Maximum | Mean | SD |
| 0-15 hrs | ~1021 | 812 | 706 | 97 | Recirculatory Mode | | |
| 16-38 hrs | 309 | 785 | 439 | 198 | 19.7 | 10.5 | 5.2 |
| 39-62 hrs | 87 | 400 | 262 | 114 | 6.9 | 5.3 | 3.0 |
| 0-62 hrs | 1417 | 812 | 568 | 450 | 19.7 | 7.9 | 4.9 |

The following reference is to be considered as included herein by reference:

Ates S., Elibol M. and Mavituna F. (1997) Production of actinorhodin by *Streptomyces coelicolor* in batch and fed-batch cultures; *Process Biochem* 32: 273-278.

The invention claimed is:

1. A membrane bioreactor comprising:
    a first fluid distribution chamber having a perforated distribution plate;
    a first fluid collection chamber having a perforated collection plate;
    a plurality of conduits in fluid communication between the first fluid distribution chamber and the first fluid collection chamber;
    a skin defining a lumen between the chambers, the lumen having a volume; and
    a plurality of axially extended distributors arranged symmetrically, adjacent and substantially parallel to the conduits to distribute a second fluid amongst the conduits between the first fluid distribution chamber and the first fluid collection chamber in a direction transverse to a longitudinal axis of the conduits, wherein
    the distributors include a series of outlets located along the length of the distributors and wherein the outlets are dimensioned such that substantially equal exit velocities of the second fluid from the distributors is effected across the outlets,
    the perforated distribution plate, the perforated collection plate, the conduits and the axially extended distributors comprise a removable insert, and
    the distributors, outlets, conduits, and skin are arranged with respect to each other to result in a local mean age of exiting second fluid molecules from the bioreactor are within approximately 7 to 10 seconds of each other at a linear second fluid velocity equivalent to one lumen volume entering and exiting per minute.

2. A membrane bioreactor according to claim 1 wherein the conduits are membrane conduits.

3. A membrane bioreactor according to claim 1 wherein a first end of the conduits are adapted to engage with the first fluid distribution chamber and the second end of the conduits are adapted to engage with the first fluid collection chamber.

4. A membrane bioreactor according to claim 1 wherein the first fluid is a liquid.

5. A membrane bioreactor according to claim 1 wherein the second fluid is a gas.

6. A membrane bioreactor according to claim 1 wherein the distributors extend between the first fluid distribution chamber and the first fluid collection chamber.

7. A membrane bioreactor according to claim 1 including at least three distributors.

8. A membrane bioreactor according to claim 1 including a second outer skin.

9. A membrane bioreactor according to claim 8 wherein the outer skin is adapted to receive temperature modifying fluids in a space between the two skins.

10. A membrane bioreactor according to claim 1 including spacer bars separating the first fluid distribution chamber from the first fluid collection chamber.

11. A membrane bioreactor according to claim 1 wherein the membrane reactor includes a frame and the insert is adapted to engage with the frame of the bioreactor.

12. A bioreactor according to claim 1 wherein the membrane conduits are comprised of a polymer material or a ceramic material.

* * * * *